United States Patent

Kanga

Patent Number: 5,160,739
Date of Patent: Nov. 3, 1992

[54] COSMETIC COMPOSITION

[75] Inventor: Vispi Kanga, Shelton, Conn.

[73] Assignee: Chesebrough-Pond's USA Co., Division of Conopco, Inc., Greenwich, Conn.

[21] Appl. No.: 758,651

[22] Filed: Sep. 12, 1991

[51] Int. Cl.$^5$ ............................................. A61K 7/02
[52] U.S. Cl. ................................. 424/401; 424/78.03; 514/844; 514/846; 514/847; 514/938; 514/939
[58] Field of Search .................. 424/401, 78.02, 78.03, 424/59, 63; 514/844, 846, 847, 937, 938, 939

[56] References Cited

U.S. PATENT DOCUMENTS

| | | | |
|---|---|---|---|
| 4,828,837 | 5/1989 | Uster et al. | 424/450 |
| 4,919,934 | 4/1990 | Deckner et al. | 424/401 |
| 5,011,681 | 4/1991 | Ciotti et al. | 252/174.15 |

OTHER PUBLICATIONS

Oil of Olay Water-Rinsable Cold Cream.
Pond's Cold Cream Water-Rinsable Cleanser.
Technical Bulletin for Macol 57.
Technical Bulletin for Emery Brand Polydecene Data Sheet 650.

*Primary Examiner*—Thurman K. Page
*Assistant Examiner*—James M. Spear
*Attorney, Agent, or Firm*—Milton L. Honig

[57] ABSTRACT

A cosmetic oil and water emulsion is described whose essential components are a polyalphaolefin and a coupling-solubilizing agent of the formula:

$$HO-CH_2CHRO)_m(CH_2)_n(OCHRCH_2)_{m'}OH$$

wherein m and m' are integers greater than 1, n is an integer greater than 3; and R is selected from the group consisting of hydrogen, $C_1$-$C_{12}$ alkyl and mixtures thereof.

7 Claims, No Drawings

COSMETIC COMPOSITION

BACKGROUND OF THE INVENTION

1. Field of the Invention

The invention concerns a cosmetic composition of the oil and water emulsion type for application to human skin.

2. The Related Art

Skin requires a certain amount of moisture to maintain a good feel and an aesthetically pleasing appearance. Water is lost through evaporation and through contact with harsh chemicals such as soaps and detergents. Dryness in skin can be overcome by application of moisturizing agents through the vehicle of a cosmetic composition.

Some types of cosmetic compositions are formulated with cleansers having the mission to remove make-up, sebum, grime and oil from face and throat. Properly formulated cleansers will quickly and efficiently remove previously applied face powder, rouge, foundation bases, cake make-up and lipstick.

Presently there are on the market a number of cleanser products, especially of the water rinseable variety. For instance, Pond's (ex Chesebrough-Pond's USA) is a cold cream brand that includes water, mineral oil, PEG-16 soya sterol, beeswax, PEG-8 dilaurate, behenic acid, cetearyl alcohol, ceteareth 20, ceresin, sodium borate and minor additives. Another product, Oil of Olay (ex Procter & Gamble) is a cold cream whose ingredients include water, mineral oil, polyalphaolefin, glycerin, isododecane, sorbitan stearate, cyclomethicone, caprylic/capric triglyceride, hexylene glycol, PEG-8 laurate, cetearyl alcohol, ceteareth 20, lauryl glycoside and various other minor components Often the components necessary to achieve moisturization have some incompatibility with components required for cleansing. These incompatibilities manifest themselves in such disadvantages as product greasiness and dermal irritation. For instance, traditional cold cream is extremely greasy in feel. Water rinseable versions of cold cream such as those mentioned above are of considerably less greasiness but still could be improved. Additionally, there may arise the problems of physical aesthetics where the formulation becomes insufficiently viscous or phase separation occurs between water and oil.

Accordingly, it is an object of the present invention to provide a cosmetic composition which imparts the dual advantages of a cleanser and moisturizer.

It is another object of the present invention to provide a cosmetic composition that is relatively non-greasy and free of mineral or vegetable oil.

It is a further object of the present invention to provide a cosmetic composition of adequate viscosity and phase stability between water and oil components.

It is still a further object of the present invention to provide a cosmetic composition that functions as a cleanser and moisturizer while being relatively non-irritating to skin.

These and other objects of the present invention will become more apparent with reference to the following summary and detailed description.

SUMMARY OF THE INVENTION

A cosmetic oil and water emulsion is provided comprising:

(i) from about 20 to about 80% water;
(ii) from about 1 to about 50% polyalphaolefin of viscosity from about 0.1 to about 10 cst;
(iii) from about 0.1 to about 10% of a coupling-solubilizing agent having the formula:

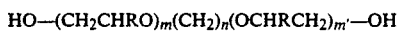

HO—(CH$_2$CHRO)$_m$(CH$_2$)$_n$(OCHRCH$_2$)$_{m'}$—OH wherein m and m' are integers greater than 1, n is an integer greater than 3; and R is selected from the group consisting of hydrogen, C$_1$–C$_{12}$ alkyl and mixtures thereof.

DETAILED DESCRIPTION

It has been found that a combined cleanser and moisturizer formulation can be achieved in the absence of any mineral oil or vegetable oil through a combination of an aqueous emulsion of polyalphaolefin combined with a coupling-solubilizing agent. The coupling-solubilizing agent has the formula:

HO—(CH$_2$CHRO)$_m$(CH$_2$)$_n$(OCHRCH$_2$)$_{m'}$—OH wherein m and m' are integers ranging anywhere from 2 to 100, preferably from 3 to 20, optimally between 4 and 8; n is an integer ranging from 4 to 20, preferably between 4 and 10, optimally from 4 to 6; and R is selected from the group consisting of methyl and hydrogen.

The coupling-solubilizing agent may be seen as formed from the alkoxylation of a C$_4$–C$_{20}$ alkylene diol. Ethylene oxide and propylene oxide are the preferred alkoxylating units. Preferred diols are 1,4-butanediol, 1,5-pentanediol, 1,6-hexanediol and 1,12-dodecanediol. A particularly preferred coupling-solubilizing agent is PPG-10 butanediol (CTFA nomenclature) available from PPG-Mazer Chemicals Inc. under the trademark Macol 57.

Coupling-solubilizing agents of the invention will be present in amounts from about 0.1 to about 10%, preferably from about 0.5 to about 5%, optimally between about 1 and 3% by weight.

The compositions of the present invention also essentially comprise one or more of a polyalphaolefin of the formula:

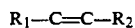

R$_1$—C=C—R$_2$ wherein R$_1$ and R$_2$ are independently selected from about C$_{20}$ to about C$_{70}$ alkyl, preferably from about C$_{20}$ to about C$_{50}$, more preferably from about C$_{30}$ to about C$_{50}$, and most preferably from about C$_{30}$ to about C$_{40}$.

Useful polyalphaolefins have an average molecular weight of from about 300 to about 800 daltons, and viscosity of from about 2 to about 10 centistokes at 100° C. The viscosity can be measured by means of a glass capillary viscometer as set forth in ASTM method D-88.

Preferably, the polyalphaolefins have a molecular weight ranging from about 445 to about 645 daltons, and a viscosity ranging from about 4 to about 8 centistokes at 100° C.; and most preferably, a molecular weight of from about 445 to about 555 daltons and a viscosity of from about 2 to about 4 centistokes at 100° C. The polyalphaolefins are available, for example, from the Ethyl Corporation as Ethylflo 162, Ethylflo 164 and Ethylflo 180 in the form of polydecenes.

Polyalphaolefins will be present from about 1 to about 50%, preferably from about 2 to about 25%, optimally between about 5 and about 15% by weight.

Relative ratio of polyalphaolefin to coupling-solubilizing agent will range from about 100:1 to about 1:20, preferably from about 20:1 to about 1:10, optimally from about 8:1 to about 1:2.

Compositions of the present invention also require the presence of water in an amount of from about 20% to about 80%, preferably between about 25 and about 50%, optimally between about 30 and about 40% by weight.

Emollient materials in the form of silicone oils and synthetic esters may be incorporated into compositions of the present invention. Amounts of the emollient may range anywhere from about 0.1 to about 75%, preferably from about 1% to about 50%, optimally between about 5 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Examples of preferred volatile silicone oils useful herein include: Dow Corning 344, Dow Corning 345 and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

Non-volatile silicone oils useful as an emollient material include polyalkyl siloxanes, polyalklyaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company).

Compositions of the present invention may also include a quaternary ammonium functionalized phosphate ester. These phosphate esters may conform to the following general formula:

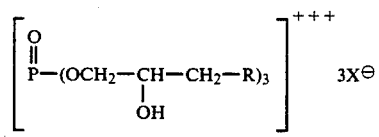

wherein R is a quaternary ammonium radical having from about 6 to about 40 carbons. This carbon atom limitation serves to include only materials of significant hydrophobic properties. The R radical can be cyclic or non-cyclic, aliphatic, aromatic or heterocyclic. X is an anion, such as halide, e.g., chloride. These phosphate esters are available from Mona Industries under the designation, Phospholipid PTC, PTD, PTS and EFA. Amounts of the quaternary phosphate ester may range from 0.1 to about 30%, optimally between about 2 and 10% by weight of the composition.

Compositions of the present invention may also include cationic polysaccharides. These materials are derived from the naturally occurring polysaccharides or those modified by etherification which are quaternized with a nitrogen-containing compound and alkylated with a compound, including a nitrogen-containing compound, containing a hydrophobe. Particularly preferred are polymeric quaternary ammonium salts of hydroxyethylcellulose reacted with a fatty alkyldimethyl ammonium substituted epoxide. An example of such material is Quatrisoft LM-200, a product of the Union Carbide Corporation. Amount of the cationic polysaccharide would normally range from about 0.1 to about 10%, preferably between 0.2 and 1% by weight of the composition.

Synthetic esters are a further category of emollients which may be included within compositions of the invention. These esters may be selected from alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

Among the ester emollients are:

(1) Alkenyl esters of fatty acids having 10 to 20 carbon atoms. Examples thereof include oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mon- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterols esters, of which cholesterol fatty acid esters are examples thereof.

Most preferred from the foregoing list of esters are propylene glycol dipelargonate and cetyl octanoate.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerol. The amount of humectant may range anywhere from 0.5 to 20%, preferably between 1 and 15% by wight of the composition.

The emulsions of the invention can also include thickeners/viscosifiers in amounts up to about 5% by weight of the composition. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses, and cross-lined acrylic acid polymers such as those sold by B. F. Goodrich under the Carbopol trademark.

Compositions of the present invention may also include emulsifiers or surfactants which may be of the nonionic, anionic, cationic or amphoteric type. Although the quaternary ammonium functionalized phosphate esters are intended as the primary emulsifier and surfactant for system of this invention, there may also be present nonionic emulsifiers. Examples of satisfactory nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono and di-fatty acid esters of ethylene glycol wherein the fatty acid moiety contains from 10 to 20 carbon atoms, fatty acid monoglyceride wherein the fatty acid moiety contains from 10 to 20 carbon atoms, diethylene glycol, polyethylene glycols of molecular weight 200 to 6000, propylene glycol of molecular weight 200 to 3000, polyoxyethylene sorbitol, polyoxypropylene sorbitan, and hyrophilic wax esters. Amounts of the emulsifier may range anywhere from about 0.1 to about 20% by weigh of the emulsion, preferably from about 2 to about 10% by weight.

Contemplated within the scope of this invention are emulsions in the form of lotions and creams where the water phase is either continuous or discontinuous. The amounts of these phases may range from about 99:1 to 1:99 by weight.

Among other skin benefit agents which may be present in the compositions of this invention are fatty acids and alcohols having from 10 to 20 carbon atoms. Suitable examples of the fatty acids include pelargonic, lauric, myristic, palmitic, stearic, isostearic, hydroxystearic, oleic, linoleic, ricinoleic, arachidic, behenic, and erucic acids. Examples of satisfactory fatty alcohols include lauryl, myristyl, cetyl, hexadecyl, stearyl, isostearyl, hydroxystearyl, oleyl, ricinoleyl, behenyl, erucyl, and 2-octyl dodecanyl alcohols. These materials may be present in amounts anywhere from about 0.1 to about 20% by weight of the composition.

Preservatives can desirably be incorporated into the cosmetic compositions of this invention to protect against the growth of potential harmful microorganisms. While it is in the aqueous phase that microorganisms tend to grow, microorganisms can also reside int eh oil phase. As such, preservatives which have solubility in both water and oil are preferably employed in the present compositions. Suitable traditional preservatives for compositions of this invention are alkyl esters of parahydroxybenzoic acid. Other preservatives which have more recently come into use include hydantoin derivatives, proprionate salts, and a variety of quaternary ammonium compounds. Cosmetic chemists are familiar with appropriate preservatives and routinely choose them to satisfy the preservative challenge test and to provide product stability. Particularly preferred preservatives are methylparaben, imidazolidinyl urea, sodium dehydroxyacetate, propylparaben and benzyl alcohol. The preservative should be selected having regard for the use of the composition and possible incompatibilities between the preservative and other ingredients in the emulsion. Preservatives are preferably employed in amounts ranging from about 0.01% to about 2% by weight of the composition.

Minor adjunct ingredients may also include fragrances, antifoam agents, opacifiers and colorants, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

A cosmetic composition illustrative of the present invention is outlined in Table I.

TABLE I

| Components | Wt % |
| --- | --- |
| Phase A | |
| Polyalphaolefin (3.8 cSt) | 10.00 |
| Propylene Glycol Dipelargonate | 4.00 |
| Cetyl Octanoate | 4.00 |
| PPG 10 Butanediol | 2.00 |
| Stearyl Alcohol | 1.40 |
| Ceteareth-20 | 0.60 |
| Decaglyceryl Diisostearate | 1.50 |
| Propylparaben | 0.10 |
| Phase B | |
| Water | 14.40 |
| Methylparaben | 0.15 |
| Disodium EDTA | 0.10 |
| Glycerin | 2.00 |
| Diglycerin | 2.00 |
| Borax | 1.40 |
| Phase C | |
| Water | 25.00 |
| Phase D | |
| Carbopol 934 (2% Soln.) | 31.00 |
| Phase E | |
| Benzyl Alcohol | 0.20 |
| Phase F | |
| Fragrance | 0.15 |

The formulation of Table I was prepared first by heating Phase A to 180° F. In a separate vessel, Phase B was heated to 160°-165° F. Phases B and C were then added to Phase A forming a mixture which was agitated for about 5 minutes. Thereafter, Phase D was added and the resultant batch agitated until a uniform consistency was obtained (about 30 minutes). Slowly the batch was cooled and thereafter Phases E and F were combined therein. Cooling was terminated when the batch reached 90° F. whereupon product was withdrawn from the mixing vessel.

EXAMPLE 2

Another cosmetic composition illustrative of the present invention is outlined in Table II. Preparation of this composition was similar to that as outlined under Example 1.

TABLE II

| Components | Wt % |
|---|---|
| Water, Deionized | 67.00 |
| Glycerin | 15.00 |
| Polyalphaolefin (4 cSt) | 4.00 |
| Cetyl Octanoate | 3.00 |
| Phospholipid PTS[1] | 3.00 |
| Stearyl Alcohol | 2.50 |
| PPG-10 Butanediol | 2.00 |
| Glyceryl Stearate | 1.50 |
| Silicone Fluid 200 | 1.00 |
| Polyquaternium-24 (Quatrisoft LM-200)[2] | 0.25 |
| Glydant | 0.25 |
| Methylparaben | 0.15 |
| Titanium Dioxide WA[3] | 0.10 |
| Propylparaben | 0.10 |
| Simethicone[4] | 0.005 |

[1]Phosphate Tris Alkylamido Tri Quaternary Compound (Mona Industries) having CTFA designation: Stearamidopropyl PG-Dimonium Phosphate
[2]Alkyl Substituted Water-Soluble Cationic Polysaccharide (Union Carbide)
[3]Water Dispersible TiO₂ (Whittaker, Clark and Daniels)
[4]Simethicone Emulsion (Dow Corning)

EXAMPLE 3

Effects of the coupling-solubilizing agent were evaluated in a base formula which is identified in Table III.

TABLE III

| Components | Base Formula Wt % |
|---|---|
| Water | 40.85 |
| Carbopol 934 (2% in water) | 31.00 |
| Polyalphaolefin (3.8 cSt) | 18.00 |
| Glycerin | 2.00 |
| Diglycerin | 2.00 |
| Stearyl Alcohol | 1.40 |
| Borax | 1.40 |
| Ceteareth-20 | 0.60 |
| Benzyl alcohol | 0.20 |
| Fragrance | 0.20 |
| Methylparaben | 0.15 |
| Propylparaben | 0.10 |
| Disodium EDTA | 0.10 |

A pair of compositions were prepared using the base formula. One of the compositions incorporated hexylene glycol and the other incorporated PPG-10 butanediol as coupling-solubilizing agents. These compositions were subjected to a series of three freeze/thaw cycles to evaluate phase stability. In this test the compositions were subjected to travel between −18° C. and 22° C. for each cycle.

TABLE IV

| Coupling-Solubilizing Agent | Wt % | Freeze/Thaw Stability |
|---|---|---|
| Hexylene glycol | 2.00 | Separated phases |
| PPG-10 Butanediol | 2.00 | Remained homogeneous |

Based on the results listed in Table IV, it is concluded that hexylene glycol does not operate as a coupling-solubilizing agent for systems whose major components are water and polyalphaolefin. On the other hand, PPG-10 Butanediol was an effective coupling-solubilizing agent.

EXAMPLE 5

A series of further experiments were conducted to evaluate freeze/thaw stability in systems with and without PPG-10 Butanediol. These experiments are outlined under Table V.

TABLE V

| Components | Formulations A | B | C |
|---|---|---|---|
| Water | 66.85 | 68.85 | 66.85 |
| Glycerin | 15.00 | 15.00 | 15.00 |
| Polyalphaolefin (100 cSt) | 4.00 | — | — |
| Polyalphaolefin (3.8 cSt) | — | 4.00 | 4.00 |
| Phospholipid PTS | 3.00 | 3.00 | 3.00 |
| Cetyl Octanoate | 3.00 | 3.00 | 3.00 |
| Stearyl Alcohol | 2.50 | 2.50 | 2.50 |
| PPG-10 Butanediol | 2.00 | — | 2.00 |
| Decaglyceryl Diisostereate | 1.50 | 1.50 | 1.50 |
| Silicone Fluid 200 | 1.00 | 1.00 | 1.00 |
| Quatrisoft LM-200 | 0.25 | 0.25 | 0.25 |
| Glydant | 0.25 | 0.25 | 0.25 |
| Methylparaben | 0.15 | 0.15 | 0.15 |
| Fragrance | 0.15 | 0.15 | 0.15 |
| Propylparaben | 0.10 | 0.10 | 0.10 |
| Titanium Dioxide | 0.10 | 0.10 | 0.10 |
| Freeze/Thaw Stability: | Stable | Separated | Stable |
| Skin feel: | Greasy afterfeel | — | Non-greasy afterfeel |

From the results of Table V, it is evident that a coupling agent such as PPG-10 Butanediol is necessary for phase stability. Advantageously, it is also seen that polyalphaolefin of higher viscosity undesirably imparts a relatively greasier afterfeel than the afterfeel exhibited by lower viscosity polyalphaolefin.

EXAMPLE 6

In this Example there is illustrated the effects of various alkoxylated and non-alkoxylated glycols.

TABLE VI

| Components | Formulations A | B | C | D |
|---|---|---|---|---|
| Water | 66.995 | 68.995 | 66.995 | 66.995 |
| Glycerin | 15.00 | 15.00 | 15.00 | 15.00 |
| Polyalphaolefin (3.8 cSt) | 4.00 | 4.00 | 4.00 | 4.00 |
| Phospholipid PTS | 3.00 | 3.00 | 3.00 | 3.00 |
| Cetyl Octanoate | 3.00 | 3.00 | 3.00 | 3.00 |
| Stearyl Alcohol | 2.50 | 2.50 | 2.50 | 2.50 |
| Hexylene Glycol | 2.00 | — | — | — |
| 1,3-Butylene Glycol | — | 2.00 | — | — |
| PPG-5-Buteth-7 (Ucon 50-HB-70) | — | — | 2.00 | — |
| PPG-14-Butyl Ether (Ucon LB-165) | — | — | — | 2.00 |
| Decaglyceryl Diisostearate | 1.50 | 1.50 | 1.50 | 1.50 |
| Silicone Fluid 200 | 1.00 | 1.00 | 0.25 | 0.25 |
| Quatrisoft LM-200 | 0.25 | 0.25 | 0.25 | 0.25 |
| Glydant | 0.25 | 0.25 | 0.25 | 0.25 |
| Methylparaben | 0.15 | 0.15 | 0.15 | 0.15 |
| Fragrance | 0.15 | 0.15 | 0.15 | 0.15 |
| Propylparaben | 0.10 | 0.10 | 0.10 | 0.10 |
| Titanium Dioxide | 0.10 | 0.10 | 0.10 | 0.10 |
| Freeze/Thaw Stability: | Separated | Separated | Stable | Stable but Grainy |

From the results of Table VI, it is seen that hexylene glycol and 1,3-butylene glycol are unsuitable as coupling-solubilizing agents.

The foregoing description and examples illustrate selected embodiments of the present invention. In light thereof, various modifications will be suggested to one skilled in the art, all of which are within the spirit and purview of this invention.

What is claimed is:

1. A cosmetic oil and water emulsion comprising:
   (i) from about 20 to about 80% water;
   (ii) from about 1 to about 50% polyalphaolefin of viscosity from about 0.1 to about 10 cst. at 100° C.;
   (iii) from about 0.1 to about 10% of a coupling-solubilizing agent which having the formula:

$$HO-(CH_2CHRO)_m(CH_2)_n(OCHRCH_2)_{m'}-OH$$

wherein m and m' are integers greater than 1, and n is an integer greater than 3; and R is selected from the group consisting of hydrogen, $C_1-C_{12}$ alkyl and mixtures thereof.

2. An emulsion according to claim 1 wherein mineral oil is present in an amount no higher than 5% by weight of the composition.

3. An emulsion according to claim 1 wherein said coupling-solubilizing agent is derived from alkoxylation of a $C_4-C_{12}$ alkanediol.

4. An emulsion according to claim 3 wherein said coupling-solubilizing agent is derived from propoxylation of butanediol.

5. An emulsion according to claim 4 wherein said coupling-solubilizing agent is PPG 10 butanediol.

6. An emulsion according to claim 1 further comprising from about 0.1 to about 30% of a quaternary ammonium functionalized phosphate ester.

7. An emulsion according to claim 1 further comprising from about 0.1 to about 10% of a cationic polysaccharide.

* * * * *